US010898418B2

(12) United States Patent
Valsesia et al.

(10) Patent No.: US 10,898,418 B2
(45) Date of Patent: Jan. 26, 2021

(54) COSMETIC COMPOSITION

(71) Applicant: INTERCOS S.p.A., Milan (IT)

(72) Inventors: Patrizia Valsesia, Calco LC (IT); Gaetano Distefano, Bergamo (IT)

(73) Assignee: INTERCOS S.P.A., Milan (IT)

( * ) Notice: Subject to any disclaimer, the term of this patent is extended or adjusted under 35 U.S.C. 154(b) by 0 days.

(21) Appl. No.: 15/324,051

(22) PCT Filed: Jul. 6, 2015

(86) PCT No.: PCT/EP2015/065343
§ 371 (c)(1),
(2) Date: Jan. 5, 2017

(87) PCT Pub. No.: WO2016/005320
PCT Pub. Date: Jan. 14, 2016

(65) Prior Publication Data
US 2017/0157004 A1    Jun. 8, 2017

(30) Foreign Application Priority Data
Jul. 9, 2014    (IT) .......................... MI2014A001252

(51) Int. Cl.
*A61K 8/25* (2006.01)
*A61K 8/26* (2006.01)
*A61Q 1/04* (2006.01)
*A61Q 1/08* (2006.01)
*A61Q 1/10* (2006.01)
*A61K 8/98* (2006.01)
*A61K 8/02* (2006.01)
*A61K 8/46* (2006.01)
*A61K 8/49* (2006.01)
*A61K 8/41* (2006.01)
*A61K 8/19* (2006.01)
*A61K 8/58* (2006.01)
*A61K 8/81* (2006.01)
*A61K 8/85* (2006.01)
*A61K 8/92* (2006.01)

(52) U.S. Cl.
CPC .............. *A61K 8/25* (2013.01); *A61K 8/022* (2013.01); *A61K 8/19* (2013.01); *A61K 8/26* (2013.01); *A61K 8/416* (2013.01); *A61K 8/466* (2013.01); *A61K 8/4946* (2013.01); *A61K 8/585* (2013.01); *A61K 8/8182* (2013.01); *A61K 8/85* (2013.01); *A61K 8/92* (2013.01); *A61K 8/927* (2013.01); *A61K 8/987* (2013.01); *A61Q 1/04* (2013.01); *A61Q 1/08* (2013.01); *A61Q 1/10* (2013.01); *A61K 2800/43* (2013.01)

(58) Field of Classification Search
None
See application file for complete search history.

(56) References Cited

U.S. PATENT DOCUMENTS

| 4,167,422 | A |  | 9/1979 | Bellanca et al. | |
|---|---|---|---|---|---|
| 6,143,280 | A |  | 11/2000 | Pike et al. | |
| 2002/0141958 | A1 | * | 10/2002 | Maio | .................... A61K 8/8152 424/63 |
| 2004/0213747 | A1 | * | 10/2004 | Patil | ..................... A61K 8/8135 424/63 |
| 2009/0280147 | A1 | * | 11/2009 | Alberius | ................. A61K 8/11 424/401 |

FOREIGN PATENT DOCUMENTS

| EP | 1 226 811 | | 7/2002 | |
|---|---|---|---|---|
| FR | 2 985 181 | | 7/2013 | |
| JP | 55139314 | A * | 10/1980 | ............... A61K 8/26 |

OTHER PUBLICATIONS

Database GNPD [Online] MINTEL; Sep. 1, 2012 (Sep. 1, 2012), "Airbrush", XP002736714, Database accession No. 1861143, Description & Ingredients.
Maria Roulia et al., "Interactions between C.I. Basic Blue 41 and aluminosilicate sorbents", Journal of Colloid and Interface Science, Academic Press, New York, NY, US, vol. 291, No. 1, Nov. 1, 2005, pp. 37-44, XP005086635.
International Search Report dated Sep. 3, 2015 in International Application No. PCT/EP2015/065343.
Written Opinion of the International Searching Authority dated Sep. 3, 2015 in International Application No. PCT/EP2015/065343.
Written Opinion of the International Preliminary Examining Authority dated Jun. 1, 2016 in International Application No. PCT/EP2015/065343.
International Preliminary Report on Patentability dated Oct. 25, 2016 in International Application No. PCT/EP2015/065343.
Applicant's Reply to Written Opinion dated Aug. 30, 2016.

* cited by examiner

*Primary Examiner* — Lakshmi S Channavajjala
(74) *Attorney, Agent, or Firm* — Wenderoth, Lind & Ponack, L.L.P.

(57) ABSTRACT

The present invention relates to an anhydrous colored cosmetic powder comprising at least one natural or synthetic silicate and at least one dye. During its preparation, such a powder may have contacted an aqueous phase which has subsequently been dried and is not present in its final state. The present invention also relates to a cosmetic composition comprising an aqueous phase and a non-aqueous phase comprising at least one colored powder portion, where the colored powder portion comprises at least one natural or synthetic silicate and at least one dye.

10 Claims, No Drawings

COSMETIC COMPOSITION

FIELD OF THE INVENTION

The present invention relates to a cosmetic composition comprising an aqueous solution and a powder portion; the present invention further relates to said powder portion, to methods of preparation thereof and to its use in said cosmetic composition.

BACKGROUND ART

In the field of cosmetics, there is a variety of products for the aesthetics of the face, lips, eyes, eyelashes, nails and the like. Some of such products, such as facial powders like eye shadows, blushers and powders, can be made with various types of powder, such as pressed powders, baked powders, gelled powders or powders which become smooth to the touch. Other products, such as nail polishes or lipsticks, are semi-liquid or pasty products able to be applied to the parts concerned (nails, lips) by a simple contact therewith.

Such cosmetic products can be produced in a wide range of colors according to the user's needs. In the cosmetic field, dyes are usually used which are soluble and/or insoluble in the medium but dispersible therein, such as pigments and lakes.

Pigments mainly consist of inorganic salts or oxides and such materials can be optically transparent (white pigments) or with absorption of a part of the visible spectrum (colored pigments). In the class of pigments, a particular category are pearly reflections pigments in which, depending on the composition, the light can be absorbed or not by a colored component (e.g. iron oxides) and can be reflected in all or some spectral components due to a thin-film interference from a transparent oxide deposited on an inert sheet (e.g. mica). Such pigments are generally used in decorative products for the face and the area around the eyes (powder and eye shadows) and in other powder preparations.

Lakes, on the other hand, typically consist of water-soluble salts of organic dyes precipitated on inorganic supports (e.g. alumina, barium sulfate, etc.); such salts formed by a precipitation reaction are often used in cosmetics. In fact, lakes typically offer a brighter and more intense color compared to inorganic pigments and a fair stability and for this they are widely used in cosmetics.

However, the solubility of organic lakes which in any case is not null at room temperature and neutral pH, increases in the presence of high temperatures and/or basic or acid pH and/or in the presence of other solutes (e.g. salts dissociated in water, such as NaCl), causing the staining of the aqueous phase, with the generation of a solution of the dye compound dissociated in water.

This can cause serious problems, such as that of color migration ("bleeding") in aqueous systems because of the partial solubility of lakes.

Such an effect can cause an unsightly skin staining due to the absorption of the dye into the epidermis when the cosmetic containing the lake is applied, making it difficult to remove it, if not mechanically, and with aggressive and irritating solvents.

Other highly undesirable effects are color inhomogeneities which are found by the consumer when using the cosmetic product (be it in powder form or in aqueous solution) and which are unacceptable in the final product due to the precipitation of the dye dissolved in different points of the product itself.

These negative effects make lakes unusable to date, except in small percentages, in all those cosmetic products that at any stage of their production process include the passage from an aqueous phase, thus considerably limiting the range of colors.

The inability to produce certain colors is much felt in the cosmetic field by the consumer, who must be able to choose the color of the cosmetic based on seasonal trends, in combination with any other fashion accessory.

Although in other industrial sectors (e.g. inks, plastics, wall paints, rubbers, etc.) similar problems have been solved successfully, for example by protecting the dye from the surrounding environment, in the cosmetics industry no solution to the problem has yet been found to date.

It is important to bear in mind that the raw materials which can be used in cosmetics must be accompanied by numerous in-vivo and in-vitro tests which verify safety for skin contact, greatly limiting the use of most raw materials which can be used in other industrial sectors in which regulations are less strict.

The main difficulty to devise the solution proposed herein therefore is to find a raw material already usable in the cosmetic field but with more features, and "change" the use thereof to make it fit for the purpose. For example phyllosilicates, or layered silicates, are known in the art as rheology modifiers or as thickening agents, i.e. which are able to impart a semi-solid gel structure to oils or water by modifying the rheological behavior, for example by increasing the viscosity of emulsions and thereby facilitating the application thereof. Based on the amount of rheology modifier added to the liquid, the final product will be more or less consistent.

Moreover, accepted dyes are also limited by the cosmetic regulations, by application area, making the study and the development of the solution to the problem extremely more complicated.

Therefore, there is the need to obtain a cosmetic composition which is able to prevent such a color migration.

It is a first object of the present invention to obtain a colored powder cosmetic composition in which lakes can be introduced in high percentages without incurring unacceptable aesthetic defects.

It is a second object of the present invention to obtain a method of preparation for obtaining a uniform color powder which does not cause color migration upon contact with water.

It is a third object of the present invention to generate pure color pigments ensuring a color purity higher than the simple mixing of traditional pigments.

It is a fourth object of the present invention to obtain a powder composition consisting of one powder portion serving as a substrate (e.g. natural or synthetic talc or mica sheets) on which a powder portion layer is evenly applied with good adhesion, able to selectively capture and immobilize the organic dye when this is present in aqueous environment.

Therefore, it is a fifth object of the present invention to obtain a cosmetic composition comprising an aqueous solution and a powder portion comprising a dye, where such a powder portion is able to selectively capture and immobilize the dye released when said powder portion comes into contact with an aqueous solution, thus preventing the color migration.

It is a sixth object of the present invention to obtain a cosmetic composition comprising an aqueous solution and a powder portion comprising a dye, where such a powder portion, before coming into contact with said aqueous solution of the cosmetic composition, has already been in contact with an aqueous solution so as to selectively capture and immobilize the dye released from said powder portion, thus preventing the color migration.

It is a further object of the present invention to maintain the sensory profile of the cosmetic products examined, where while the introduction of an absorbing system corrects the color migration, it should not alter the pleasantness to the touch of the formulation when taking the product and applying it to the skin.

The Applicant noted that it is possible to obtain a cosmetic composition comprising an element which prevents the color migration.

SUMMARY OF THE INVENTION

In a first aspect thereof, the present invention relates to a colored powder cosmetic composition like that indicated in claim 1.

In fact, the Applicant of the present application has surprisingly found that a colored powder cosmetic composition comprising at least one natural or synthetic silicate and at least one dye, where said at least one silicate is able to absorb the water-soluble portion of said dye released from the dye itself when it is in contact with an aqueous solution, is able to prevent the above migration phenomenon.

In fact, when said colored powder comes in contact with an aqueous phase, the water-soluble portion of the dye released therefrom is absorbed by said at least one natural or synthetic silicate; therefore, such a water-soluble portion of the dye is retained and will tend no more to migrate and stain the elements with which it may come into contact.

In the description of the present invention and in the appended claims, the term "silicate" means the class of (natural or synthetic) inorganic compounds mainly consisting of silicon and oxygen and based on anionic tetrahedral units of the $[SiO_4]^{4-}$ type organized according to variable architectures and the charge of which is neutralized by metal cations.

Such tetrahedral units can remain isolated (as in the so-called nesosilicate) or, by sharing oxygen atoms, connect to form structures of various types, as in soro-, cyclo-, ino-, phyllo- or tecto-silicates: the substitution of (tetravalent) silicon atoms with (trivalent) aluminum atoms allows the entry of positive ions in the framework, such as, e.g., in tectosilicates.

Preferably, said at least one silicate is a phyllosilicate (also called layered silicate), which has a lamellar or scaly appearance, with well-defined flaking. The phyllosilicates are based on indefinitely flanking extended chains of tetrahedrons $[SiO_4]^{4-}$, joined together, on the same plane, to form layers which are repeated regularly along the direction perpendicular to the plane itself.

Phyllosilicates (or layered silicates) may be of natural origin, i.e. extracted from rocks present in natural environments, or they may be obtained through chemical synthesis starting from inorganic precursors (sol-gel or hydrothermal synthesis).

Such phyllosilicates can be further modified by including organic compounds within the structure which give them an oleophilic character.

Preferably, said at least one natural or synthetic phyllosilicate is a sepiolite, hectorite, montmorillonite, bentonite-based phyllosilicate or mixtures thereof.

Preferably, said at least one natural or synthetic phyllosilicate is a phyllosilicate comprising a quaternary salt of sepiolite, hectorite, montmorillonite, bentonite or mixtures thereof. Suitable quaternary salts may be, for example, ammonium, disteardimonium, stearalkonium, phosphonium, arsonium, benzalkonium, cetrimonium, pyridinium, tiazonium salts and the like. More preferably, said at least one natural or synthetic phyllosilicate is a phyllosilicate which comprises stearalkonium bentonite and/or hectorite.

Examples of modified phyllosilicate oleophils useful for the present invention are benzalkonium montmorillonite (available from Southern Clay Products under the trade name Garamite®7305 (mixture)), quaternium-90 montmorillonite (available from Southern Clay Products under the trade name Garamite®7303 (mixture)), disteardimonium hectorite (available from Element Specialities under the trade name Bentone®38 V), stearalkonium hectorite (available from Element Specialities under the trade name Bentone®V 27), benzalkonium sepiolite (available from Southern Clay Products under the trade name Garamite®7305 (mixture)), quaternio-90 sepiolite (available from Southern Clay Products under the trade name Garamite®7303 (mixture)), stearalkonium bentonite (available from Southern Clay Products under the trade names of Claytone AF, Garamite®VT, Tixogel® LG, Tixogel® LG-M, Tixogel® MP-250, Tixogel® VZ, Tixogel® VZ-V, and from Bentec S.p.A. under the trade names of Viscogel B3, Viscogel B4, Viscogel B7, Viscogel B8, Viscogel ED, Viscogel GM, Viscogel S4, Viscogel SD).

In the description of the present invention and in the appended claims, the term "dye" shall mean any ingredient capable of imparting color to the formulation.

Dyes can be distinguished in pure dyes soluble in water (water-soluble) and insoluble in water. Water-soluble dyes are mainly soluble salts of organic dyes or organic dyes with polar groups. Water-insoluble dyes are referred to as pigments; pigments are further subdivided into inorganic pigments (e.g. iron oxides, titanium dioxide, dichromium trioxide, ferric ferrocyanide, etc.) and organic pigments (water insoluble salts of organic chromophores).

Particular types of organic pigments useful for the present invention are lakes, constituted starting from said pure water-soluble dyes precipitated as insoluble salts on insoluble inorganic substrates, such as for example on talc, aluminum hydrate, calcium carbonate, sulphate barium substrates, and the like. Such lakes, when such substrates are precipitated on such insoluble inorganic substrates, form insoluble products with pigmentary properties, that is, they color by "contact" dispersing in the application medium. Compared to pure water-soluble dyes from which they originate, lakes possess a better resistance to light and their coloring strength depends on the degree of fineness of the particles: the higher the degree of grinding, the higher the coloring strength and the smaller the amount of product to use.

Other particular types of pigments useful for the present invention are the so-called "beads", which are pearlescent pigments consisting of crystals in the form of thin flakes, with high refractive index, particularly used in decorative cosmetics. Such pearlescent pigments have a core of mica, or aluminum and potassium silicate, on which titanium dioxide and optionally metal oxides are layered/deposited. Varying the titanium dioxide thickness gives beads of different grain size and more or less colored and opaque reflections.

Examples of pure water-soluble dyes particularly useful for the purposes of the present invention, while not being limited thereto, are those selected from the group comprising Yellow 5 (CAS #1934-21-0), Yellow 6 (CAS #2783-94-0), Yellow 7 (CAS #2321-07-5), Yellow 8 (CAS #518-47-8), Yellow 10 (CAS #8004-92-0), Orange 4 (CAS #633-96-5), Red 4 (CAS #4548-53-2), Red 22 (CAS #17372-87-1, 548-26-5), Red 28 (CAS #18472-87-2), Red 33 (CAS #3567-66-6), Red 36 (CAS #2814-77-9), Red 40 (CAS #25956-17-6), Cochineal (CAS #1343-78-8), Blue 1 (CAS #3844-45-9), Ext. Violet 2 (CAS #4430-18-6), Green 3 (CAS #2353-45-9), Green 5 (CAS #4403-90-1), Green 8 (CAS #6358-69-6).

Examples of non water-soluble organic pigments extended on inorganic supports (lakes) particularly useful for the purposes of the present invention, while not being limited thereto, are those selected from the group comprising Yellow 5 Lake, Yellow 6 Lake (CAS #15790-07-5), Yellow 7 Lake, Yellow 10 Lake (CAS #68814-04-0), Orange 4 Lake, Red 4 Lake, Red 22 Lake, Red 28 Lake, Red 33 Lake, Red 36 Lake), Red 40 Lake (CAS #84455-18-5), Carmine (CAS #1390-65-4), Blue 1 Lake (CAS #15792-67-3, 68921-42-6), e Green 3 Lake.

Preferably, said powder cosmetic composition comprises particles having an average size <150 μm, more preferably <50 μm, even more preferably <5 μm.

Preferably, said colored powder cosmetic composition comprises at least one silicate, preferably a natural or synthetic phyllosilicate in an amount from 50% to 90% by weight, more preferably from 55% by weight to 85% by weight, even more preferably from 60% by weight to 80% by weight and most preferably from 65% by weight to 75% by weight, and at least one dye preferably in an amount from 10% to 50% by weight, more preferably from 15% to 45% by weight, even more preferably from 20% to 40% by weight and most preferably from 25% to 35% by weight.

Preferably, said powder cosmetic composition further comprises at least one portion of cosmetic excipient, selected from the group comprising, for example, sericite (which is a silicate of aluminum and potassium, also called natural mica), fluorophlogopite (also called synthetic mica), borosilicate, talc, boron nitride, silica, alumina, etc. More preferably, said cosmetic excipient is natural mica or synthetic mica.

If said powder cosmetic composition further comprises said cosmetic excipient portion, preferably said colored powder composition comprises at least one silicate, preferably a natural or synthetic phyllosilicate in an amount from 3% to 80% by weight, more preferably from 3% to 50% by weight, even more preferably from 5% to 30% by weight and most preferably from 5% to 15% by weight, a cosmetic excipient, preferably natural mica or synthetic mica, in an amount preferably from 50% to 99% by weight, more preferably from 55% to 95% by weight, even more preferably from 60% to 90% by weight and most preferably from 65% to 85% by weight, and a lake, preferably in an amount from 0.1% to 40% by weight, more preferably from 1% to 30% by weight, even more preferably from 2% to 20% by weight and most preferably from 2.5% to 10% by weight.

Preferably, said colored powder cosmetic composition according to the first aspect of the present invention may be used in any anhydrous product used in cosmetics, such as in a powder, face powder, blusher, pencil and the like.

Some embodiments of said colored powder cosmetic composition will now be described.

In a first embodiment, said colored powder cosmetic composition is obtained by the dry mixing of an insoluble dye with said at least one silicate, preferably an either natural or synthetic phyllosilicate.

In this way, said colored powder cosmetic composition was obtained by dry mixing the ingredients, i.e. without the use of aqueous solutions. Therefore, when said colored powder cosmetic composition is contact with an aqueous solution for the first time, the silicate, preferably a natural or synthetic phyllosilicate, contained in such a colored powder cosmetic composition will prevent the migration of the water-soluble portion of the dye contained in the powder.

Preferably, in said colored powder cosmetic composition obtained according to said first embodiment, said at least one silicate, preferably a natural or synthetic phyllosilicate, is a phyllosilicate comprising stearalkonium bentonite and/or hectorite; preferably, said dye is a lake.

Preferably, in said colored powder cosmetic composition obtained according to said first embodiment, said at least one silicate, preferably a natural or synthetic phyllosilicate is in an amount from 20% to 95% by weight, more preferably from 40% to 90% by weight, even more preferably from 50% to 85% by weight and most preferably from 60% to 85% by weight; preferably, said dye (lake) is in an amount from 5% to 80% by weight, more preferably from 10% to 60% by weight, even more preferably from 15% to 50% by weight and most preferably from 15% to 40% by weight.

In this way, it is possible to obtain a colored powder cosmetic composition in which lakes can be introduced even in high percentages without incurring unacceptable aesthetic defects.

Said colored powder cosmetic composition obtained according to said first embodiment is particularly useful for the preparation of cosmetic compositions such as cosmetic powders of the blusher, foundation, powder type.

In a second embodiment, said colored powder cosmetic composition of the present invention is obtained by: a) first dissolving said dye in an aqueous solution, such as for example in distilled water, and adding to such a solution so obtained said at least one silicate, preferably a natural or synthetic phyllosilicate, so as to obtain a liquid colored dispersion of silicate, preferably of phyllosilicate and dye; and, then, b) filtering said liquid dispersion of a silicate, preferably phyllosilicate, and dye and leaving it to dry to obtain a powder with low residual water, such as for example <1%.

In this way, in this second embodiment, said colored powder cosmetic composition is obtained, first, by contacting said dye with an aqueous solution, thus giving the possibility that as a result of such a contact, the above-mentioned problem of migration of the water-soluble portion of the dye could occur, but in fact preventing the occurrence thereof thanks to the presence of said at least one silicate, preferably a natural or synthetic phyllosilicate, which is capable of absorbing said water-soluble dye portion and, then, drying and filtering said liquid dispersion of silicate, preferably phyllosilicate, and the water-soluble dye portion, obtaining again a colored powder. Such colored powder thus obtained again is more effective than the same colored powder obtained according to the first embodiment of the powder described above (which had not been subjected to a first contact with an aqueous solution and subsequent drying) since, the dye having already been subjected to migration in the step of preparation of the powder, its water-soluble portion will not tend to migrate anymore when placed in contact for a second time with an aqueous solution.

Preferably, in said second embodiment of said colored powder cosmetic composition, said at least one silicate, preferably a natural or synthetic phyllosilicate, is a phyllosilicate comprising stearalkonium bentonite and/or hectorite; preferably, said dye is a water-soluble pure dye.

Preferably, in said colored powdered cosmetic composition obtained according to said second embodiment, said liquid colored dispersion of silicate, preferably phyllosilicate, and dye obtained at the end of said step a) described above comprises water in an amount from 5% to 95% by weight, more preferably from 20% to 90% by weight, even more preferably from 40% to 85% by weight and most preferably from 60% to 80% by weight, at least one silicate, preferably a natural or synthetic phyllosilicate, preferably in an amount from 5% to 95% by weight, more preferably from 10% to 80% by weight, even more preferably from 15% to 60% by weight and most preferably from 20% to 40% by weight, and said dye preferably in an amount from 0.01% to 20% by weight, more preferably from 0.1% to 15% by weight, even more preferably from 0.3% to 10% by weight and most preferably from 0.5% to 5% by weight.

Therefore, said colored powder cosmetic composition initially had an aqueous phase which was dried and thus is not present in its final state.

Said colored powder cosmetic composition obtained according to said second embodiment is particularly useful for the preparation of cosmetic compositions such as eye shadows.

In a third embodiment, said colored powder cosmetic composition is obtained by absorbing a water-soluble fraction of dye released from a lake. Such a lake, initially in the form of powder mixed with a suitable amount of a silicate, preferably a natural or synthetic phyllosilicate, is wetted so as to give an aqueous dispersion of a silicate, preferably phyllosilicate, and of a water-soluble fraction of dye released from the lake, such as to enable the silicate, preferably a natural or synthetic phyllosilicate, to absorb such a water-soluble fraction of dye released from said lake. The dispersion is then filtered and dried to obtain a colored powder with low residual water, such as for example <1%.

Therefore, also in this case, similar to that described above with reference to the second embodiment, the colored powder cosmetic composition is obtained by contacting a fraction of water-soluble dye (in this case released from a lake) with a silicate, preferably phyllosilicate, in water and then drying such a solution again to obtain again a colored powder which has already operated to prevent migration. Also in this case, there will thus be no further possibility of migration of the water-soluble portion of the dye (lake) contained in the colored powder cosmetic composition when this will be in contact with an aqueous solution.

Preferably, in said third embodiment of said colored powder cosmetic composition, said at least one silicate, preferably a natural or synthetic phyllosilicate, is a phyllosilicate comprising stearalkonium bentonite and/or hectorite.

Preferably, in said colored powder cosmetic composition obtained according to said third embodiment, said aqueous dispersion of silicate, preferably of phyllosilicate and lake, described above comprises water, preferably in an amount from 5% to 95% by weight, more preferably from 20% to 90% by weight, even more preferably from 40% to 85% by weight and most preferably from 50% to 80% by weight, at least one silicate, preferably a natural or synthetic phyllosilicate, preferably in an amount from 5% to 95% by weight, more preferably from 10% to 80% by weight, even more preferably from 15% to 60% by weight and most preferably from 30% to 50% by weight, and said lake preferably in an amount from 0.1% to 40% by weight, more preferably from 1% to 30% by weight, even more preferably from 3% to 20% by weight and most preferably from 5% to 15% by weight.

Said colored powder cosmetic composition obtained according to said third embodiment is especially useful for the preparation of cosmetic compositions, such as eye shadows, cosmetic inks for the decoration of the eyelids, mascara for the decoration of the eyelashes, cosmetic fluid for the lips, and pencils and eyeliners for the decoration of the eyes.

In a fourth embodiment, said colored powder cosmetic composition comprises at least one silicate, preferably a natural or synthetic phyllosilicate, and at least one dye and at least one cosmetic excipient portion.

Preferably, in said fourth embodiment of said colored powder cosmetic composition, said at least one silicate, preferably a natural or synthetic phyllosilicate, is a phyllosilicate comprising stearalkonium bentonite and/or hectorite; preferably, said dye is a lake; and preferably, said cosmetic excipient is selected from the group comprising, for example, sericite (which is an aluminum and potassium silicate also called natural mica), fluorophlogopite (also called synthetic mica), borosilicate, talcum, boron nitride, silica, alumina, etc.

Preferably, in this fourth embodiment, said colored powder cosmetic composition is obtained by dry mixing said at least one lake with a powder based on said at least one silicate, preferably a natural or synthetic phyllosilicate, and said cosmetic excipient portion (e.g. natural mica or synthetic mica).

Preferably, said colored powder cosmetic composition mixture comprises at least one silicate, preferably a natural or synthetic phyllosilicate, preferably in an amount from 3% to 80% by weight, more preferably from 3% to 50% by weight, even more preferably from 5% to 30% by weight and most preferably from 5% to 15% by weight, a cosmetic excipient, preferably natural mica or synthetic mica, in an amount preferably from 50% to 99% by weight, more preferably from 55% to 95% by weight, even more preferably from 60% to 90% by weight and most preferably from 65% to 85% by weight, and a lake, preferably in an amount from 0.1% to 40% by weight, more preferably from 1% to 30% by weight, even more preferably from 2% to 20% by weight and most preferably from 2.5% to 10% by weight.

Said colored powder cosmetic composition obtained according to said fourth embodiment is particularly useful for the preparation of cosmetic compositions such as eye shadows and cosmetic emulsions for the decoration of the eyes.

In a second aspect thereof, the present invention relates to a cosmetic composition comprising an aqueous phase like that indicated in claim 9.

In fact, the Applicant of the present application has surprisingly found that a cosmetic composition comprising an aqueous phase and a non-aqueous phase comprising at least one colored powder portion, where said colored powder portion comprises at least one natural or synthetic silicate, and at least one dye, where said at least one silicate is able to absorb the water-soluble portion of said dye released from said powder when it is in contact with said aqueous solution, is able to prevent the above color migration problem.

In fact, when said colored powder comes into contact with said aqueous phase of the cosmetic composition, the water-soluble dye portion released from the powder is absorbed by said at least one natural or synthetic silicate, preventing the migration of color.

Preferably, the cosmetic composition according to the second aspect of the present invention can be any product used in cosmetics, such as nail polishes and solvents thereof, mascara, foundation, marker pens, eye shadows, lipsticks, lip gloss, as well as oil/silicone in water emulsions and water in oil/silicone emulsions, or other products comprising an aqueous phase for the care and the aesthetics of fingernails, face, eyes, lips and body products in general.

Preferably, said at least one natural or synthetic silicate is a natural or synthetic phyllosilicate.

Preferably, said at least one silicate, preferably a natural or synthetic phyllosilicate, and said dye contained in said colored powder portion are a silicate, preferably a phyllosilicate, and a dye, respectively, as described above with reference to the first aspect of the present invention referred to a colored powder cosmetic composition.

In particular, preferably, said at least one phyllosilicate which comprises stearalkonium bentonite; moreover, preferably, said dye is a lake.

Preferably, said cosmetic composition according to the second aspect of the present invention, consists of said aqueous phase in an amount from 5% to 95% by weight, preferably from 10% to 90% by weight, more preferably from 20% to 80% by weight, even more preferably from 30% to 70% by weight and most preferably from 40% to 60% by weight, and of said non-aqueous phase in an amount from 5% to 95% by weight, preferably from 10% to 90% by weight, more preferably from 20% to 80% by weight, even more preferably from 30% to 70% by weight and most preferably from 40% to 60% by weight.

Preferably, said non-aqueous phase comprises said at least one colored powder portion based on at least one silicate, preferably a natural or synthetic phyllosilicate, and at least one dye, where said powder portion is in an amount from 1% to 99% by weight, preferably from 10% to 90% by weight and most preferably from 20% to 80% by weight of such a non-aqueous phase.

Preferably, said colored powder portion comprises a silicate, preferably a natural or synthetic phyllosilicate, in an amount from 50% to 90% by weight, more preferably from 55% by weight to 85% by weight, even more preferably from 60% by weight to 80% by weight and most preferably from 65% by weight to 75% by weight, and at least one dye preferably in an amount from 10% to 50% by weight, more preferably from 15% to 45% by weight, even more preferably from 20% to 40% by weight and most preferably from 25% to 35% by weight.

Preferably, said colored powder portion contained in the cosmetic composition according to the second aspect of the present invention, can be obtained according to any of the methods of preparation described above with reference from the first to the fourth embodiment of said colored powder cosmetic composition according to the first aspect of the present invention.

Preferably, said colored powder portion is obtained by: a) dissolving said dye in distilled water and adding said at least one silicate, preferably a phyllosilicate, so as to obtain a dispersion of silicate, preferably of phyllosilicate, and dye; and by b) filtering said dispersion and leaving it to dry to obtain a powder having a water residual <1%.

In this way, when said colored powder portion prepared with said method is inserted in said cosmetic composition comprising an aqueous phase according to the second aspect of the present invention, the dye contained in the powder portion, the water-soluble portion of which has already been in contact with said aqueous solution during the preparation of the colored powder, will no longer be subject to a new episode of migration when it is in contact with said aqueous phase of the cosmetic composition.

Preferably, said cosmetic composition according to the second aspect of the present invention may be in liquid, semi-liquid or pasty form.

Preferably, said cosmetic composition according to the second aspect of the present invention further comprises at least one among solvents, silicone compounds, waxes, cosmetics excipients, film-forming polymers, texturizers, emollients, preservatives, perfumes, flavors, vitamins, antioxidants, oils or vegetable or mineral fats, surfactants or mixtures thereof.

Particularly suitable solvents can be any organic solvent suitable for use in cosmetic products, such as for example aliphatic hydrocarbons having from 6 to 20 carbon atoms, preferably from 8 to 16 carbon atoms, as well as as isoparaffins such as isooctane, isononane, isodecane, isododecane.

Particularly suitable silicone compounds can be, for example, polisiloxanes, cyclomethicone, dimethicone.

Particularly suitable waxes can be, for example, candelilla wax, carnauba wax, beeswax, ceresin, microcrystalline wax, paraffin wax, silicone wax, polyethylene wax and the like.

Particularly suitably cosmetic excipients can be talc, mica, silica, kaolin, zinc oxide, calcium carbonate, magnesium phosphate carbonate, starch and derivatives thereof, nylon, polyethylene, acrylic (co)polymers and so on.

Particularly suitable film-forming polymers may be lipophilic (co)polymers derived from, for example, polyvinylpyrrolidone, fluorine-containing monomers, acrylic monomers, cellulose, etc.

Particularly suitable texturizers may be, for example, polyurethanes, polyethylene, HDI/trimethylol hexyllactone crosspolymer, boron nitride, dimethicone, nylon-12 and others.

Particularly suitable emollients or emulsifiers may be octyl dodecanol, dimethicone, isononyl isononanoate, dipentaerythrityl pentaisononanoate.

Particularly suitable surfactants may be sorbitan stearate, sorbitan palmitate, sorbitan laurate and polyoxyethylenes derived from such compounds.

In a third aspect thereof, the present invention relates to a method for preparing a colored powder composition comprising at least one silicate, synthetic or natural, and at least one dye.

The Applicant of the present invention has in fact surprisingly found that a method for preparing a colored powder composition comprising at least one natural or synthetic silicate and at least one dye, method comprising the steps of:

a) dissolving said dye in an aqueous solution and adding said at least one silicate, obtaining a silicate and dye dispersion; and b) filtering said dispersion and allowing it to be dried to obtain a powder with water residual <1%, allows, thanks to the presence of said at least one silicate, synthetic or natural, preventing the problem of migration as a result of the contact between the water-soluble portion of said dye and said aqueous solution during the step of preparation of the powder itself.

Moreover in this way, when the powder containing the dye prepared with said method is inserted in a cosmetic composition comprising an aqueous phase, said dye, the water-soluble portion of which has already been in contact with said aqueous solution during the preparation of the powder, will no longer be subject to a new episode of migration when it is in contact with said aqueous phase of the cosmetic composition.

Preferably, said at least one natural or synthetic silicate, and said dye contained in said colored powder portion are a silicate and a dye, respectively, as described above with reference to the first aspect of the present invention referred to a colored powder cosmetic composition.

In particular, preferably, said at least one silicate is a phyllosilicate which comprises stearalkonium bentonite; moreover, preferably, said dye is a lake.

Preferably, the aqueous solution indicated in step b) above is distilled water.

Preferably, during said step a), said silicate dispersion, preferably of phyllosilicate, and dye thus obtained is left under stirring for about one hour at room temperature.

Preferably, during said step b), said dispersion is filtered at reduced pressure and then washed with plenty of distilled water on paper filter before being subjected to drying.

Preferably, said drying takes place by placing the powder recovered from said filtration in a furnace at a temperature from about 60° C. to 90° C., preferably at 80° C. up to have a residual content of water <1%.

Preferably, the amount of such a water residual content is verified using a thermobalance.

Preferably, at the end of the above step b), said method further comprises the further step of c) grinding the powder thus dried for obtaining particles having average size <150 μm, for example using a 150 mesh metal sieve; more preferably, for obtaining particles having average size <50 μm, even more preferably <5 μm.

Preferably, in said step a), said dispersion of silicate, preferably of phyllosilicate, and dye in aqueous solution comprises water in an amount from 5% to 95% by weight, more preferably from 20% to 90% by weight, even more preferably from 40% to 85% by weight and most preferably from 60% to 80% by weight, at least one silicate, preferably a natural or synthetic phyllosilicate, in an amount from 5% to 95% by weight, more preferably from 10% to 80% by weight, even more preferably from 15% to 60% by weight and most preferably from 20% to 40% by weight, and at least one dye, preferably in an amount from 0.01% to 20% by weight, more preferably from 0.1% to 15% by weight, even more preferably from 0.3% to 10% by weight and most preferably from 0.5% to 5% by weight.

Alternatively, the colored powder composition comprising at least one silicate, preferably a natural or synthetic phyllosilicate, and at least one dye can be prepared by dry mixing said at least one silicate, preferably a natural or synthetic phyllosilicate, and at least one dye; preferably, said dye being a lake. Preferably, said dry mixing takes place by means of a mixer for powders for about 5 minutes. Preferably, said dry-mixed colored powder composition comprises said at least one silicate, preferably a natural or synthetic phyllosilicate, in an amount from 20% to 95% by weight, more preferably from 40% to 90% by weight, even more preferably from 50% to 85% by weight and most preferably from 60% to 85% by weight; preferably, said dye (lake) is in an amount from 5% to 80% by weight, more preferably from 10% to 60% by weight, even more preferably from 15% to 50% by weight and most preferably from 15% to 40% by weight.

In a fourth aspect thereof, the present invention relates to a method for preparing a colored powder composition comprising at least one natural or synthetic silicate, by the absorption of the dye portion released from a lake in aqueous environment.

The Applicant of the present invention has in fact surprisingly found that a method for preparing a colored powder composition comprising at least one natural or synthetic silicate, the method comprising the steps of:

a) mixing a powder lake and said at least one natural or synthetic silicate;

b) ensuring that said mixture of step a) above is in contact with an aqueous solution to form a dispersion in an aqueous environment containing a water-soluble fraction of the dye released from said lake;

c) allowing said at least one natural or synthetic silicate to absorb said water-soluble fraction of the dye released from said lake;

d) drying what obtained to obtain a colored powder having a water residual <1%, allows obtaining a colored powder comprising at least one natural or synthetic silicate, and preventing any subsequent migration problem due to contact between said colored powder thus obtained and an aqueous solution contained in a cosmetic composition in which said colored powder will be introduced.

Moreover in this way, similar to the method of preparation of the powder according to the third aspect of the present invention described above, when the lake prepared with said method is inserted in a cosmetic composition comprising an aqueous phase, said lake, having already released a water-soluble portion of dye following the contact with said aqueous solution during the preparation of the powder, will no longer be subject to a new episode of migration when it is in contact with said aqueous phase of the cosmetic composition.

Preferably, said at least one natural or synthetic silicate contained in said colored powder portion is a silicate, as described above with reference to the first aspect of the present invention referred to a colored powder cosmetic composition. In particular, preferably, said at least one silicate is a phyllosilicate and more preferably a phyllosilicate comprising stearalkonium bentonite.

Preferably, the aqueous solution indicated in step b) above is distilled water.

Preferably, before said step d) of drying, said silicate dispersion, preferably of phyllosilicate, and water-soluble dye portion released from said lake is left under stirring for about one hour at room temperature. Preferably, moreover, thereafter, said dispersion is filtered at reduced pressure and then washed with plenty of distilled water on paper filter before being subjected to drying.

Preferably, said step d) of drying takes place by placing the powder recovered from said filtration in a furnace at a temperature from about 60° C. to 90° C., preferably at 80° C. up to have a residual content of water <1%.

Preferably, the amount of such a water residual content is verified using a thermobalance.

Preferably, at the end of the above step d) of drying, said method further comprises the further step of e) grinding the powder thus dried for obtaining particles having average size <150 μm, for example using a 150 mesh metal sieve; more preferably, for obtaining particles having average size <50 μm, even more preferably <5 μm.

Preferably, said silicate dispersion, preferably of phyllosilicate, and lake in aqueous solution comprises at least one silicate, preferably a natural or synthetic phyllosilicate, preferably in an amount from 5% to 95% by weight, more preferably from 10% to 80% by weight, even more preferably from 15% to 60% by weight and most preferably from 30% to 50% by weight, at least one lake, in an amount preferably from 0.1% to 40% by weight, more preferably from 1% to 30% by weight, even more preferably from 3% to 20% by weight and most preferably from 5% to 15% by weight, and water, preferably in an amount from 5% to 95% by weight, more preferably from 20% to 90% by weight, even more preferably from 40% to 85% by weight and most preferably from 50% to 80% by weight.

In a fifth aspect thereof, the present invention relates to a method as that indicated in claim 18 for preparing a colored powder composition comprising at least one natural or synthetic silicate, at least one dye and at least one cosmetic excipient portion.

The Applicant of the present invention has in fact surprisingly found that a method for preparing a colored powder composition comprising at least one natural or synthetic silicate, at least one dye and at least one cosmetic excipient portion, the method comprising the steps of:

a) homogeneously and uniformly mixing at least one natural or synthetic silicate and a hydrocarbon solvent;

b) depositing the obtained mixture on a support of cosmetic excipient to let said support of cosmetic excipient soaking said mixture;

c) activating the exfoliation of said support of cosmetic excipient soaked with said mixture by means of alcohol or any other analogous activator in order to obtain a gel;

d) drying the gel up to obtain a powder with a residual content of said hydrocarbon solvent <1%;

e) dry mixing said powder so obtained with a lake, is able to provide a colored powder which also has the feature of an adsorbent material made of natural or synthetic silicate to be exfoliated up to its constituent units, i.e. the single sheets of silicate.

Preferably, said at least one natural or synthetic silicate contained in said colored powder portion is a silicate, as described above with reference to the first aspect of the present invention referred to a colored powder cosmetic composition. In particular, preferably, said at least one silicate is a phyllosilicate, preferably it comprises stearalkonium bentonite.

Preferably, said cosmetic excipient is selected from the group comprising, for example, sericite (which is a silicate of aluminum and potassium, also called natural mica), fluorophlogopite (also called synthetic mica), borosilicate, talc, boron nitride, silica, alumina, etc. More preferably, said cosmetic excipient is natural mica or synthetic mica.

Preferably, said step a) of mixing occurs under continuous stirring at room temperature.

Preferably, said hydrocarbon solvent in step a) is an isododecane.

Preferably, said step c) of activating the exfoliation of the mixture impregnated with cosmetic excipient takes place by means of alcohol, such as for example ethyl alcohol or isopropyl alcohol, or any analogous activator, such as for example propylene carbonate or glycerin carbonate.

Preferably, said step d) of drying takes place by placing the gel so obtained in a furnace at a temperature from about 60° C. to 90° C., preferably at 80° C. up to have a residual content of isododecane <1%.

Preferably, the amount of such a isododecane residual content is verified using a thermobalance.

Preferably, at the end of the above step d) of drying and before said step e), said method further comprises the further step of d') grinding the gel thus dried for obtaining particles having average size <150 μm, for example using a 150 mesh metal sieve; more preferably, for obtaining particles having average size <50 μm, even more preferably <5 μm.

Preferably, said mixture comprising at least one silicate, preferably a natural or synthetic phyllosilicate, a hydrocarbon solvent and a cosmetic excipient comprises at least one silicate, preferably a natural or synthetic phyllosilicate, preferably in an amount from 0.1% to 30% by weight, more preferably from 1% to 20% by weight, even more preferably from 2% to 15% by weight and most preferably from 3% to 10% by weight, at least one hydrocarbon solvent, in an amount preferably from 15% to 75% by weight, more preferably from 20% to 70% by weight, even more preferably from 25% to 65% by weight and most preferably from 30% to 60% by weight, and a cosmetic excipient, preferably natural or synthetic mica, preferably in an amount from 15% to 75% by weight, more preferably from 20% to 70% by weight, even more preferably from 25% to 65% by weight and most preferably from 30% to 60% by weight.

Preferably, said step e) of dry-mixing of the powder obtained above with a lake takes place by means of a powder mixer for a period of about 5 minutes.

Preferably, said colored powder composition obtained with the method described above comprises at least one silicate, preferably a natural or synthetic phyllosilicate, preferably in an amount from 2% to 35% by weight, more preferably from 3% to 30% by weight, even more preferably from 4% to 25% by weight and most preferably from 5% to 20% by weight, a cosmetic excipient, preferably natural mica or synthetic mica, in an amount preferably from 60% to 98% by weight, more preferably from 65% to 95% by weight, even more preferably from 70% to 95% by weight and most preferably from 75% to 90% by weight, and a lake, preferably in an amount from 0.1% to 20% by weight, more preferably from 1% to 15% by weight, even more preferably from 2% to 10% by weight and most preferably from 2.5% to 8% by weight.

Preferably, said method according to the fifth aspect of the present invention comprises, at the end of said step c) of exfoliation, a further step of reconversion in which it is possible to convert the gel obtained into a solid material (silicate, preferably phyllosilicate). This further step preferably takes place when said solvent is a volatile solvent, for example isododecane.

More preferably, said reconversion takes place in the presence of another solid finely dispersed in the gel, such as an excipient powder.

In this way, the deposition of the silicate, preferably phyllosilicate, on such an excipient is obtained, with the advantage that the final powder is a composite powder which benefits both from the particle size features of the excipient (sophisticated cosmetic properties) and of the absorbent capacity of the silicate, preferably of the phyllosilicate.

In a sixth aspect thereof, the present invention relates to the use of a colored powder composition for the preparation of a cosmetic composition as that indicated in claim 21.

The Applicant of the present application has in fact surprisingly found that the use of a colored powder composition comprising at least one natural or synthetic silicate and at least one dye, for the preparation of a cosmetic composition comprising an aqueous phase, allows said at least one natural or synthetic silicate to absorb the water-soluble portion of said at least one dye when said colored powder comes in contact with said aqueous phase of said cosmetic composition.

The above mentioned problem of "migration" is thus solved, in particular when said colored powder is inserted in a cosmetic composition.

Moreover, thanks to the plasticity of the silicate used in the preparation of the powders of the present invention, it was possible to modulate the texture of the pigment and its adhesion to the silicate.

Preferably, said at least one natural or synthetic silicate contained in said colored powder portion is a silicate, as described above with reference to the first aspect of the present invention referred to a colored powder cosmetic composition. In particular, preferably, said at least one silicate is a phyllosilicate, preferably it comprises stearalkonium bentonite.

Further features and advantages of the present invention will appear more clearly from the following detailed description of preferred but non-exclusive embodiments thereof, made by way of a non limiting example.

DETAILED DESCRIPTION

The following detailed description relates to a particular embodiment of a composition according to the present invention.

EXAMPLES

Example 1. Preparation of the Powders

Preparation of Powder 1 (Dry Mixing).

A lake and a natural or synthetic phyllosilicate were taken. The lake was a carmine (C.I. 75470), a red pigment extracted from dried cochineal insects (scientific name *Dactylopius coccus*). The phyllosilicate was a stearalkonium hectorite, a creamy white powder, available from Elementis Specialties, Delden, Netherlands with the initials Bentone® 27 V. The two ingredients were dry mixed with a powder mixer for 5 minutes. A colored powder was thus obtained (Powder 1) with a homogeneous distribution comprising 20% by weight of the lake and 80% by weight of the natural or synthetic phyllosilicate. It was thus possible to introduce the lake in high percentages without incurring unacceptable aesthetic defects.

Preparation of Powder 2 (Absorption of the Water-Soluble Dye).

An aqueous dispersion was prepared by dissolving 0.826% by weight of the pure water-soluble dye called Blue 1 (C.I. 42090), a reddish-blue powder, in 66.116% by weight of distilled water and adding 33.058% by weight of stearalkonium hectorite to the mixture. The dispersion is left under stirring for 1 hour at room temperature and then filtered at reduced pressure and then washed with plentiful distilled water on paper filter. The powder recovered by filtration was placed to dry in an oven at 80° C. up to have a residual water content <1%, verified using a thermobalance. After drying, the powder was subjected to sifting with a 150 mesh metal sieve.

A colored powder (Powder 2) was so obtained, having an even color distribution in which the phyllosilicate absorbed the water-soluble portion of the dye. Such a powder will not be subject to the problem of migration when placed in contact with an aqueous solution and can therefore be regarded as belonging to a new class of pigments, associable to the pigment Maya Blue).

In a variant of such a method of preparation, the natural or synthetic phyllosilicates "charged" with two different pure dyes can be dry mixed and by processing such a mixture in an aqueous environment, the inter-diffusion of the dyes will lead to the creation of an end pigment having a unique color. In this way, a higher color purity than the simple mixing of traditional pigments is ensured.

Preparation of Powder 3 (Absorption of the Water-Soluble Fraction of Dye Released from a Non Water-Soluble Lake in Aqueous Environment).

10% by weight of the water-insoluble lake called Blue 1 Lake (C.I. 42090) were mixed with 40% by weight of stearalkonium hectorite. The mixture was wetted with 50% by weight of distilled water to obtain an aqueous dispersion of lake and phyllosilicate. The dispersion is left under stirring for 1 hour at room temperature and then filtered at reduced pressure and then washed with plentiful distilled water on paper filter. The powder recovered by filtration was placed to dry in an oven at 80° C. up to have a residual water content 1%, verified using a thermobalance. After drying, the powder was subjected to sifting with a 150 mesh metal sieve.

A colored powder (Powder 3) was so obtained, having an even color distribution in which the phyllosilicate absorbed the water-soluble fraction of dye released by the non water-soluble lake in aqueous environment.

Preparation of Powder 4 (Absorption of the Water-Soluble Fraction of Dye Released from a Non Water-Soluble Lake in Aqueous Environment).

Powder 4 was prepared in a manner similar to Powder 3, using a water-insoluble lake called Red 7 Lake (C.I. 15850), reddish in color, instead of the lake called Blue 1 Lake (C.I. 42090), in the same percentages by weight.

A colored powder (Powder 4) was so obtained, having an even color distribution in which the phyllosilicate absorbed the water-soluble fraction of dye released by the non water-soluble lake in aqueous environment.

Preparation of Powder 5 (Absorption of the Water-Soluble Fraction of Dye Released from a Non Water-Soluble Lake in Aqueous Environment).

Powder 5 was prepared in a manner similar to Powder 3, using a water-insoluble lake called Yellow 5 Lake (C.I. 19140), instead of the lake called Blue 1 Lake (C.I. 42090), in the same percentages by weight.

A colored powder (Powder 5) was so obtained, having an even color distribution in which the phyllosilicate absorbed the water-soluble fraction of dye released by the non water-soluble lake in aqueous environment.

Preparation of Powder 6 (Dry Mixing of the Lake with Phyllosilicate Deposited on Mica).

4.36% by weight of tearalkonium hectorite (natural or synthetic phyllosilicate) and 43.56% of isododecane (a hydrocarbon solvent) were homogeneously and uniformly mixed; the mixture was deposited on 49.92% by weight of fluorophlogopite (synthetic mica). The exfoliation of hectorite was activated with 2.16% by weight of alcohol, under continuous stirring at room temperature, so as to obtain a gel. The gel so obtained was placed to dry in an oven at 80° C. up to have a residual isododecane content <1%, verified using a thermobalance. After drying, the powder obtained, consisting of stearalkonium hectorite and synthetic mica, was subjected to sieving with a 150 mesh metal sieve. The powder thus obtained after sieving was then dry mixed with the water-insoluble lake called Blue 1 Lake (C.I. 42090) by means of a powder mixer for 5 minutes, obtaining a composite having the following proportions: 3.86% by weight of such a lake, 7.720 stearalkonium hectorite and 88.42% by weight of synthetic mica.

Example 2. Powder Evaluation Test

Powders 1 and 3 described above were evaluated by means of migration and absorption tests as described hereafter.

Some aqueous solutions of $CaCl_2$ were prepared at 5% by weight; to 20 g of each of such solutions, 0.5 g of pigment Carmine (C.I. 75470) and progressive amounts (from 0 to 4 g) of Bentone® 27 V (phyllosilicate of stearalkonium hectorite), which are the two compounds used to prepare Powder 1 mentioned above, were added. The resulting dispersions were incubated in a stove at 80° C. for 24 h to induce the migration of the organic pigment. At the end, the dispersions were filtered and the mother liquors were examined. The dye concentration was determined by HPLC.

The above test was repeated using, instead of pigment Carmine (C.I. 75470), the lake Blue 1 Lake (C.I. 42090) used to prepare Powder 3 described above.

Table 1 below shows the colors of mother liquor after testing and the residual amount of chromophore in mother liquor, expressed in parts per million (PPM).

TABLE 1

| Test | Bentone$^R$ 27 VG | Pigment g | Sol. 5% weight CaCl$_2$/g | Mother liquor color | Residual amount of chromophore in mother liquor/ppm |
|---|---|---|---|---|---|
| 1 | 0.00 | Carmine 0.50 | 20.00 | ++++ intense red | 249 |
| 2 | 0.10 | Carmine 0.50 | 20.00 | ++++ | 246 |
| 3 | 0.20 | Carmine 0.50 | 20.00 | ++++ | 21 |
| 4 | 0.50 | Carmine 0.50 | 20.00 | ++++ | 19 |
| 5 | 1.00 | Carmine 0.50 | 20.00 | ++ | 5 |
| 6 | 2.00 | Carmine 0.50 | 20.00 | + (almost clear) | <5 |
| 7 | 3.00 | Carmine 0.50 | 20.00 | clear | <5 |
| 8 | 4.00 | Carmine 0.50 | 20.00 | clear | <5 |
| 9 | 0.00 | Blue 1 Lake 0.50 | 20.00 | ++++ intense blue | 1104 |
| 10 | 0.10 | Blue 1 Lake 0.50 | 20.00 | ++++ | 987 |
| 11 | 0.20 | Blue 1 Lake 0.50 | 20.00 | ++++ | 837 |
| 12 | 0.50 | Blue 1 Lake 0.50 | 20.00 | ++++ | 465 |
| 13 | 1.00 | Blue 1 Lake 0.50 | 20.00 | ++ | 44 |
| 14 | 2.00 | Blue 1 Lake 0.50 | 20.00 | + (almost clear) | 8 |
| 15 | 3.00 | Blue 1 Lake 0.50 | 20.00 | clear | <5 |
| 16 | 4.00 | Blue 1 Lake 0.50 | 20.00 | clear | <5 |

Table 1 shows that, in the absence of Bentone® 27 V (tests 1 and 9), the color of the mother liquors was intense red or intense blue, respectively, depending on whether the test concerned the carmine or blue lake. The amount of residual chromophore in the mother liquor of such tests 1 and 9 was significantly high (about 1000 ppm). The coloring of the mother liquors decreased up to become clear by using increasing amounts of Bentone® 27 V and the amount of chromophore was reduced to a few units in ppm. Excellent results were obtained using Bentone® 27 V in amounts starting from 1 g, both in combination with carmine (tests 5-8) and with the blue lake (tests 13-16).

Example 3. Powder Evaluation Test

Powders 1 and 3 described above were evaluated by means of resistance tests to strong acids and bases and to mono- and divalent salts.

Four different samples of the invention of 1 g of composite pigment consisting of the lake Blue 1 Lake (20% by weight) and Bentone® 27 V (80% by weight), the same components used to prepare Powder 3 as described above, were each treated with 10 ml of 4 different solutions 0.1M, of HCl, NaOH, CaCl$_2$ and NaCl, respectively. The dispersion was stirred for 1 hour at room temperature. The mother liquors were filtered and the amounts of chromophore were analyzed.

Four different comparison samples were subjected to similar treatment, 1 g of the composite pigment consisting of the same lake Blue 1 Lake (20% by weight) but coated on an inert excipient (talc, 80% by weight) rather than mixed with Bentone® 27 V, in the same percentage of 80% by weight.

Table 2 below shows the colors of mother liquor after testing and the residual amount of chromophore in mother liquor, expressed in parts per million (PPM).

TABLE 2

| Test | Pigment (20% by weight) | Bentone$^R$ 27 V (80% by weight) | Talc (80% by weight) | Treatment 10 ml 0.1M | Mother liquor color | Residual amount of chromophore in mother liquor/ppm |
|---|---|---|---|---|---|---|
| 17 (inv.) | Carmine | YES | NO | NaCl | + (almost clear) | 19 |
| 18 (inv.) | Carmine | YES | NO | CaCl$_2$ | + | 19 |
| 19 (inv.) | Carmine | YES | NO | NaOH | +++ (red) | 210 |
| 20 (inv.) | Carmine | YES | NO | HCl | + | 21 |
| 21 (comp.) | Carmine | NO | YES | NaCl | +++ | 220 |
| 22 (comp.) | Carmine | NO | YES | CaCl$_2$ | ++ | 80 |
| 23 (comp.) | Carmine | NO | YES | NaOH | ++++ intense red | 3500 |
| 24 (comp.) | Carmine | NO | YES | HCl | ++ | 80 |

TABLE 2-continued

| Test | Pigment (20% by weight) | Bentone$^R$ 27 V (80% by weight) | Talc (80% by weight) | Treatment 10 ml 0.1M | Mother liquor color | Residual amount of chromophore in mother liquor/ppm |
|---|---|---|---|---|---|---|
| 25 (inv.) | Blue 1 Lake | YES | NO | NaCl | clear | <5 |
| 26 (inv.) | Blue 1 Lake | YES | NO | CaCl$_2$ | clear | <5 |
| 27 (inv.) | Blue 1 Lake | YES | NO | NaOH | + almost clear | <5 |
| 28 (inv.) | Blue 1 Lake | YES | NO | HCl | ++++ intense blue | <5 |
| 29 (comp.) | Blue 1 Lake | NO | YES | NaCl | ++++ | 192 |
| 30 (comp.) | Blue 1 Lake | NO | YES | CaCl$_2$ | ++++ | 310 |
| 31 (comp.) | Blue 1 Lake | NO | YES | NaOH | ++++ | 643 |
| 32 (comp.) | Blue 1 Lake | NO | YES | HCl | ++++ | 70 |

Table 2 shows that the tests of the invention n. 25-28, in which the lake Blue 1 Lake was combined with the phyllosilicate Bentone® 27 V, showed clear staining of the mother liquors after treatment with acids, bases or salts, and a very low amount of residual chromophore (less than 5 ppm). Conversely, the corresponding comparison tests n. 29-32, where the same Blue 1 Lake was coated on talc rather than being mixed with the phyllosilicate, the color of the mother liquors turned deep blue and the amount of residual chromophore in the mother liquors was considerably high.

Also in the similar tests n. 17-24 in which carmine was used instead of the lake Blue 1 Lake, the staining of the mother liquors and the amount of residual chromophore therein relating to the tests of the invention n. 17-20 were found to be significantly lower than the corresponding comparison tests n. 21-24, where talc was used instead of the phyllosilicate Bentone® 27 V.

Therefore, the evaluation test of powders 1 and 3 shown in examples 2 and 3 above show that, in the presence of a phyllosilicate, an excellent effect of prevention of the migration of a dye or lake is obtained when it is in contact with an aqueous solution. Conversely, the same effect is not obtained if the dye or lake is coated on a traditional excipient, such as talc, instead of being mixed with the phyllosilicate.

Example 4. Evaluation of the Powder Color

To an aqueous solution of one or more water-soluble dyes Red n. 33, Yellow n. 5 and Blue n. 1 (see Table 1), the required amount of phyllosilicate Bentone® 27 V was added. After stirring for 6 hours, the mixture was filtered and the compound left to dry at 80° C. to obtain a colored powder of the invention. The color of a pigment film thus obtained was analyzed, dispersed in castor oil, and the CIElab coordinates were obtained, which identify a color space in which each point (corresponding to a vector starting from the origin of the Cartesian axes) uniquely represents a color. The quantities defining each of these points are simply the three coordinates L*, a* and b*, each variable in a range from −100 to +100, where L* expresses the clarity of a color, where the maximum value of L* coincides with the paper white, while a* and b* define the hue of a color, where the more positive is the value of a*, the redder the color, while the more negative is the value of a*, the greener the color; similarly, the more positive is the value of b*, the yellower the color, while the more negative is the value of b*, the bluer the color.

Table 3 shows the CIElab coordinates obtained by varying the type of dye used, alone or in combination with another dye, and adjusting the percentages of dye compared with the phyllosilicate.

TABLE 3

| Test | Water-soluble dye | % dye compared to Bentone$^R$ 27 V | L* | a* | b* | Mass color |
|---|---|---|---|---|---|---|
| 33 (inv.) | Red n. 33 | 3.50 | 60.32 | 45.17 | −6.07 | Amaranth |
| 34 (inv.) | Yellow n. 5 | 0.625 | 91.69 | −4.3 | 33.07 | Yellow |
| 35 (inv.) | Yellow n. 5 | 1.25 | 91.26 | −4.26 | 39.08 | Yellow |
| 36 (inv.) | Yellow n. 5 | 2.50 | 90.31 | −3.98 | 48.69 | Yellow |
| 37 (inv.) | Blue n. 1 | 0.625 | 82.80 | −20.31 | −6.36 | Blue |
| 38 (inv.) | Blue n. 1 | 1.25 | 78.59 | −24.20 | −10.97 | Blue |
| 39 (inv.) | Blue n. 1 | 2.50 | 70.61 | −29.54 | −20.79 | Blue |

TABLE 3-continued

| Test | Water-soluble dye | % dye compared to Bentone$^R$ 27 V | L* | a* | b* | Mass color |
|---|---|---|---|---|---|---|
| 40 (inv.) | Red n. 33 + Yellow n. 5 | 1.25 (Red) + 1.25 (Yellow) | 70.40 | 30.74 | 16.68 | Tyrian purple |
| 41 (inv.) | Red n. 33 + Blue n. 1 | 1.25 (Red) + 1.25 (Blue) | 67.46 | 2.07 | −17.63 | Indigo dye |
| 42 (inv.) | Yellow n. 5 + Blue n. 1 | 1.25 (Yellow) + 1.25 (Blue) | 77.73 | −29.40 | 16.72 | Green |
| 43 (inv.) | Yellow n. 5 + Blue n. 1 | 0.625 (Yellow) + 1.875 (Blue) | 78.74 | −27.24 | 3.23 | Emerald green |
| 44 (inv.) | Yellow n. 5 + Blue n. 1 | 1.875 (Yellow) + 0.625 (Blue) | 75.08 | −31.8 | 3.6 | Pea green |

Table 3 shows that by mixing a single type of dye with the phyllosilicate, colored powders were obtained substantially of the same color as the starting dye, while mixing two types of dye, in various percentages, with the phyllosilicate, colored powders were obtained having various shades of gradations. It was therefore possible to obtain a variety of colored powders to meet the user's needs to have powders to be used in the cosmetic field with more and more varied colors.

Example 5 Photo-Stability of the Powders

Powders with similar amount of organic dye were subjected to the accelerated photo-aging Q-Sun test. In fact, pigment (A) based on the absorption of the water-soluble dye Blue n. 1 (2.4% by weight) on 97.6% by weight of phyllosilicate Bentone® 27 V was compared with a pigment (B) based on the same water-soluble dye and non-absorbent excipient (talc) instead of phyllosilicate. Once the tablet was prepared by compacting, half of it was covered with an opaque screen (aluminum sheet) and subjected to the photo-accelerated aging test. At the end, the color intensity was evaluated. Pigment (A) showed substantially the retention of a high intensity of color, while pigment (B), devoid of phyllosilicate, showed a marked decrease of such an intensity of color.

Example 6 Preparation of the Cosmetic Compositions

Powders 1-5 prepared above comprising a dye or lake and at least one phyllosilicate were used to prepare cosmetic compositions to be used as eye shadows, lipsticks, nail polishes and similar accessories useful in cosmetics.

Such powders during their preparation may have had contact with an aqueous phase which was then dried and which therefore is not present in the final state of such powders at the time of preparation of the cosmetic compositions described hereafter.

Preparation of Cosmetic Composition 1 (Blusher Cosmetic Powder).

Cosmetic composition 1 was prepared, comprising 50% by weight of an aqueous phase and 50% by weight of a non-aqueous phase compared to the total weight of the cosmetic composition.

The aqueous phase consisted of 45% by weight of water and 5% by weight of isopropyl alcohol.

The non-aqueous phase comprised:

| | |
|---|---|
| Powder 1 (see above) | 10% by weight |
| talc | 30% by weight |
| HDI/trimethylol hexyllactone crosspolymer | 1.25% by weight |

-continued

| | |
|---|---|
| magnesium aluminum silicate | 1.5% by weight |
| boron nitride | 5% by weight |
| dimethicone | 1.75% by weight |
| ethylhexylglycerin | 0.25% by weight |
| caprylyl glycol | 0.25% by weight |

The aqueous phase was then removed to obtain the blusher cosmetic powder of the Cosmetic Composition 1.

Preparation of Cosmetic Composition 2 (Eye Shadow Cosmetic Powder).

Cosmetic composition 2 was prepared, comprising 42.08% by weight of an aqueous phase and 57.92% by weight of a non-aqueous phase compared to the total weight of the cosmetic composition.

The non-aqueous phase comprised:

| | |
|---|---|
| Powder 2 (see above) | 12% by weight |
| Mica | 30% by weight |
| magnesium aluminum silicate | 1.438% by weight |
| HDI/trimethylol hexyllactone crosspolymer | 2.874% by weight |
| dimethicone | 2.76% by weight |
| isononyl isononanoate | 2.76% by weight |
| vinylpyrrolidone hexadecene copolymer | 2.76% by weight |
| cetyl PEG/PPG-10/1 dimethicone | 2.62% by weight |
| ethylhexylglycerin | 0.288% by weight |
| polysorbate 20 | 0.42% by weight |

The aqueous phase was then removed to obtain the eye shadow cosmetic powder of the Cosmetic Composition 2.

Preparation of Cosmetic Composition 3 (Eye Shadow Cosmetic Powder).

The cosmetic composition 3 was prepared in a similar way to the cosmetic composition 2, using Powder 3 in place of Powder 2, in the percentages.

Preparation of the Cosmetic Composition 4 (Cosmetic Ink for Decoration of the Eyelids (Marker)).

Cosmetic composition 4 was prepared, comprising 48.8% by weight of an aqueous phase and 51.2% by weight of a non-aqueous phase compared to the total weight of the cosmetic composition.

The non-aqueous phase comprised:

| | |
|---|---|
| Powder 3 (see above) | 7.82% by weight |
| alcohol | 7.46% by weight |
| 1.2-hexanediol | 4.46% by weight |
| sodium polyaspartate | 1.00% by weight |
| titanium dioxide | 7.79% by weight |
| acrylate copolymer | 7.18% by weight |
| preservatives | 15.49% by weight |

Preparation of the Cosmetic Composition 5 (Mascara for Decoration of the Eyelashes).

Cosmetic composition 5 was prepared, comprising 54.46% by weight of an aqueous phase and 45.54% by weight of a non-aqueous phase compared to the total weight of the cosmetic composition.

The non-aqueous phase comprised:

| | |
|---|---|
| Powder 3 (see above) | 7.34% by weight |
| butyl glycol | 2.10% by weight |
| *Senegal acacia* gum | 4.20% by weight |
| triethanolamine | 2.50% by weight |
| stearic acid | 5.04% by weight |
| synthetic beeswax | 10.50% by weight |
| paraffin | 8.40% by weight |
| polybutene | 2.10% by weight |
| ascorbyl palmitate | 0.21% by weight |
| vinylpyrrolidone/eicosene copolymer | 2.10% by weight |
| preservatives | 1.05% by weight |

Preparation of Cosmetic Composition 6 (Cosmetic Fluid for the Lips).

Cosmetic composition 6 was prepared, comprising 35.525% by weight of an aqueous phase and 64.475% by weight of a non-aqueous phase compared to the total weight of the cosmetic composition.

The non-aqueous phase comprised:

| | |
|---|---|
| Powder 4 (see above) | 7.00% by weight |
| octyldodecanol | 16.47% by weight |
| ethylcellulose | 1.83% by weight |
| dipentaerythrityl pentaisononanoate | 9.00% by weight |
| sorbitan stearate | 3.00% by weight |
| polybutene | 9.70% by weight |
| polyglyceryl-4 caprylate | 3.60% by weight |
| Xanthan gum | 0.40% by weight |
| vinylpyrrolidone/metacrylamide/vinyl imidazole copolymer | 7.00% by weight |
| denatured alcohol | 5.775% by weight |
| preservatives | 0.70% by weight |

Preparation of the Cosmetic Composition 7 (Eyeliner for Decoration of the Eyes).

Cosmetic composition 7 was prepared, comprising 35.620% by weight of an aqueous phase and 64.380% by weight of a non-aqueous phase compared to the total weight of the cosmetic composition.

The non-aqueous phase comprised:

| | |
|---|---|
| Powder 3 (see above) | 24.10% by weight |
| Powder 5 (see above) | 10.06% by weight |
| *Chondrus Crispus* | 0.34% by weight |
| glycerine | 3.81% by weight |
| polysorbate 80 | 0.45% by weight |
| polyurethane 24 | 23.52% by weight |
| preservatives | 2.10% by weight |

Preparation of Cosmetic Composition 8 (Eye Shadow Cosmetic Powder).

Cosmetic composition 8 was prepared, comprising 43.326% by weight of an aqueous phase and 56.674% by weight of a non-aqueous phase compared to the total weight of the cosmetic composition.

The non-aqueous phase comprised:

| | |
|---|---|
| Powder 6 (see above) | 20.00% by weight |
| Mica | 25.00% by weight |
| Nylon-12 | 0.595% by weight |
| magnesium aluminum silicate | 1.438% by weight |
| dimethicone | 2.083% by weight |
| vinylpyrrolidone hexadecene copolymer (polyvinylpyrrolidone/hexadecene copolymer) | 2.083% by weight |
| isononyl isononanoate | 2.38% by weight |
| cetyl PEG/PPG-10/1 dimethicone | 2.38% by weight |
| ethylhexylglycerin | 0.298% by weight |
| caprylyl glycol | 0.417% by weight |

The aqueous phase was then removed to obtain the eye shadow cosmetic powder of the Cosmetic Composition 8.

Preparation of the Cosmetic Composition 9 (Cosmetic Emulsion for Decoration of the Eyes).

Cosmetic composition 9 was prepared, comprising 35.48% by weight of an aqueous phase and 64.52% by weight of a non-aqueous phase compared to the total weight of the cosmetic composition.

The non-aqueous phase comprised:

| | |
|---|---|
| Powder 6 (see above) | 45.515% by weight |
| sorbitan stearate | 2.68% by weight |
| ascorbyl palmitate | 0.01% by weight |
| tocopherol | 0.025% by weight |
| titanium dioxide (C.I. 77891) | 14.08% by weight |
| polyarylamide | 0.56% by weight |
| preservatives | 1.65% by weight |

All compositions 1-9 of the invention thus prepared therefore contained at least one powder of the invention comprising at least one dye or lake mixed with a phyllosilicate.

Such compositions 1-9 of the invention showed no migration of the dyes contained therein, even when placed in contact with aqueous solutions. In fact, there was no migration of the color and no negative effects of unwanted staining of the skin or other parts of the body were observed after having been subjected to treatment with such compositions of the invention comprising the powders of the invention as described above.

The industrial invention has been described with reference to a preferred embodiment, but it will be understood that many modifications and variations, which will become apparent to those skilled in the art, can be made to such preferred embodiments of the cosmetic composition described and of the powder according to the present invention, still remaining within the scope of the invention itself.

Therefore, the extent and scope of the present description should not be limited by any of the exemplary embodiments described above, but should be defined only on the basis of the following claims appended hereto and their equivalents.

The invention claimed is:

1. A colored powder cosmetic composition consisting of at least one native, non-exfoliated silicate, natural or synthetic, at least one dye having an inorganic support and an aqueous solution consisting of water or a mixture of water or isopropyl alcohol, wherein said at least one native, non-exfoliated silicate is a native, non-exfoliated quaternized phyllosilicate consisting of a quaternary salt of sepiolite, hectorite, montmorillonite, bentonite or mixtures thereof, said at least one dye is extended on the inorganic support and comprises a water-soluble portion, said at least one silicate is able to absorb the water-soluble portion of said dye when the dye is in contact with the aqueous solution, said at least one silicate is in an amount from 50% to 90% by weight and said at least one dye is in an amount from 10% to 50% by weight.

2. The colored powder cosmetic composition of claim 1 wherein said at least one native, non-exfoliated silicate is in an amount from 55% to 85% by weight and said at least one dye is in an amount from 15% to 45% by weight.

3. The colored powder cosmetic composition of claim 1 wherein said at least one native, non-exfoliated silicate is in an amount from 60% to 80% by weight and said at least one dye is in an amount from 20% to 40% by weight.

4. The colored powder cosmetic composition of claim 1 wherein said at least one native, non-exfoliated silicate is in an amount from 65% to 75% by weight and said at least one dye is in an amount from 25% to 35% by weight.

5. The colored powder cosmetic composition of claim 1 wherein said quaternary salt of sepiolite, hectorite, montmorillonite, bentonite or mixture thereof is selected from the group comprising ammonium, disteardimonium, stearalkonium, phosphonium, arsonium, benzalkonium, cetrimonium, pyridinium, and tiazonium salts.

6. The colored powder cosmetic composition of claim 1 which includes particles having average size <150 µm.

7. The cosmetic composition of claim 1, wherein said powder composition is obtained by:

a) dissolving said at least one dye in distilled water and adding said at least one native, non-exfoliated silicate to obtain a silicate and dye dispersion; and b) filtering said dispersion and leaving it to dry to obtain a powder having a water residual <1%.

8. The cosmetic composition of claim 7, wherein the powder obtained at the end of step b) is sieved to obtain particles having average size <150 µm.

9. The cosmetic composition of claim 7, wherein said powder composition is obtained by:

a) mixing a powder lake and said at least one native, non-exfoliated silicate, natural or synthetic;

b) ensuring that the mixture of step a) above is in contact with an aqueous solution to form a dispersion in an aqueous environment containing a dye water-soluble lake fraction released from said powder lake;

c) allowing said at least one native, non-exfoliated silicate, natural or synthetic, to absorb said dye water-soluble lake fraction released from said powder lake;

d) drying what obtained in step c) to obtain a colored powder having a water residual <1%.

10. The cosmetic composition of claim 9, wherein the colored powder obtained at the end of step b) is sieved to obtain particles having average size <150 µm.

* * * * *